United States Patent
Beck

(10) Patent No.: US 10,016,192 B2
(45) Date of Patent: Jul. 10, 2018

(54) SUTURE FOR CONNECTING A HUMAN OR ANIMAL TISSUE, SOFT ANCHOR AND METHOD FOR ATTACHING A TISSUE TO A BONE

(71) Applicant: Tornier, Inc., Bloomington, MN (US)

(72) Inventor: Clinton Andrew Beck, Fort Wayne, IN (US)

(73) Assignee: Tornier, Inc., Bloomington, MN (US)

( * ) Notice: Subject to any disclaimer, the term of this patent is extended or adjusted under 35 U.S.C. 154(b) by 968 days.

(21) Appl. No.: 14/304,235

(22) Filed: Jun. 13, 2014

(65) Prior Publication Data

US 2014/0371792 A1 Dec. 18, 2014

Related U.S. Application Data

(60) Provisional application No. 61/835,113, filed on Jun. 14, 2013.

(51) Int. Cl.
*A61B 17/04* (2006.01)
*A61B 17/06* (2006.01)

(52) U.S. Cl.
CPC .... *A61B 17/0401* (2013.01); *A61B 17/06166* (2013.01); *A61B 2017/0403* (2013.01);
(Continued)

(58) Field of Classification Search
CPC ........ A61B 17/0401; A61B 2017/0409; A61B 2017/0446; A61B 2017/0459;
(Continued)

(56) References Cited

U.S. PATENT DOCUMENTS 1,562,543 A 11/1925 Cox
3,527,223 A 9/1970 Shein
(Continued)

FOREIGN PATENT DOCUMENTS

EP 0 673 624 9/1995
EP 0 713 683 5/1996
(Continued)

OTHER PUBLICATIONS

Duerig et al., "Metals: Superelastic Nitinol for Medical Devices", Medical Plastics and Biomaterials, Mar. 1997, in 7 pages.

*Primary Examiner* — Katherine Rodjom
(74) *Attorney, Agent, or Firm* — Knobbe, Martens, Olson & Bear, LLP

(57) ABSTRACT

Described herein is a suture for connecting a human or animal tissue comprising a suture strand, wherein at least two protrusions are provided on the suture strand, the protrusions are provided spaced apart from each other along the suture strand. Also described herein is a soft anchor, the soft anchor having a proximal end and a distal end in an insertion direction. At the proximal end and the distal end the soft anchor includes respectively at least one opening for a suture. The proximal end and the distal end of the soft anchor are connected with at least one, in particular two, connecting portions. The soft anchor has a first state, in which it is adapted to be inserted into a bore in the insertion direction, and a second state, in which it is locked in a bore. In the first state, the distal end and the proximal end defines the extension of the soft anchor in insertion direction.

26 Claims, 8 Drawing Sheets

(52) U.S. Cl.
CPC ............... *A61B 2017/0406* (2013.01); *A61B 2017/06176* (2013.01)

(58) Field of Classification Search
CPC .... A61B 2017/0461; A61B 2017/0462; A61B 2017/0464; A61B 17/06116; A61B 2017/061761
See application file for complete search history.

(56) References Cited

U.S. PATENT DOCUMENTS

| | | | |
|---|---|---|---|
| 3,716,058 A | 2/1973 | Tanner, Jr. |
| 4,170,990 A | 10/1979 | Baumgart et al. |
| 4,485,816 A | 12/1984 | Krumme |
| 4,632,100 A | 12/1986 | Somers et al. |
| 4,665,906 A | 5/1987 | Jervis |
| 4,669,473 A | 6/1987 | Richards et al. |
| 4,870,957 A | 10/1989 | Goble et al. |
| 4,898,156 A | 2/1990 | Gatturna et al. |
| 4,946,468 A | 8/1990 | Li |
| 5,002,550 A | 3/1991 | Li |
| 5,035,712 A | 7/1991 | Hoffman |
| 5,046,513 A | 9/1991 | Gatturna et al. |
| 5,141,520 A | 8/1992 | Goble et al. |
| 5,190,546 A | 3/1993 | Jervis |
| 5,192,303 A | 3/1993 | Gatturna et al. |
| 5,258,016 A | 11/1993 | DiPoto et al. |
| 5,268,001 A | 12/1993 | Nicholson et al. |
| 5,318,579 A | 6/1994 | Chow |
| 5,356,413 A | 10/1994 | Martins et al. |
| 5,358,511 A | 10/1994 | Gatturna et al. |
| 5,372,599 A | 12/1994 | Martins |
| 5,383,905 A | 1/1995 | Golds et al. |
| 5,391,173 A | 2/1995 | Wilk |
| 5,403,348 A | 4/1995 | Bonutti |
| 5,417,712 A | 5/1995 | Whittaker et al. |
| 5,486,197 A | 1/1996 | Le et al. |
| 5,505,735 A | 4/1996 | Li |
| 5,522,820 A | 6/1996 | Gaspari et al. |
| 5,522,845 A | 6/1996 | Wenstrom, Jr. |
| 5,527,343 A | 6/1996 | Bonutti |
| 5,554,171 A | 9/1996 | Gatturna et al. |
| 5,571,104 A | 11/1996 | Li |
| 5,584,835 A | 12/1996 | Greenfield |
| 5,601,557 A | 2/1997 | Hayhurst |
| 5,626,612 A | 5/1997 | Bartlett |
| 5,645,553 A | 7/1997 | Kolesa et al. |
| 5,647,874 A | 7/1997 | Hayhurst |
| 5,649,963 A | 7/1997 | McDevitt |
| 5,662,654 A | 9/1997 | Thompson |
| 5,662,657 A | 9/1997 | Carn |
| 5,681,352 A | 10/1997 | Clancy, III et al. |
| 5,702,397 A | 12/1997 | Goble et al. |
| 5,725,557 A | 3/1998 | Gatturna et al. |
| 5,766,218 A | 6/1998 | Arnott |
| 5,843,127 A | 12/1998 | Li |
| 5,876,434 A | 3/1999 | Flomenblit et al. |
| 5,893,856 A | 4/1999 | Jacob et al. |
| 5,948,001 A | 9/1999 | Larsen |
| 5,957,953 A | 9/1999 | DiPoto et al. |
| 5,964,770 A | 10/1999 | Flomenbilt et al. |
| 5,968,078 A | 10/1999 | Grotz |
| 5,972,000 A | 10/1999 | Beyar et al. |
| 5,980,558 A | 11/1999 | Wiley |
| 5,984,927 A | 11/1999 | Wenstrom, Jr. et al. |
| 6,027,523 A | 2/2000 | Schmieding |
| 6,033,430 A | 3/2000 | Bonutti |
| 6,042,583 A | 3/2000 | Thompson et al. |
| 6,066,160 A | 5/2000 | Colvin et al. |
| 6,077,216 A | 6/2000 | Benderev et al. |
| 6,113,611 A | 9/2000 | Allen et al. |
| 6,146,406 A | 11/2000 | Shluzas et al. |
| 6,200,330 B1 | 3/2001 | Benderev et al. |
| 6,210,413 B1 | 4/2001 | Justis et al. |
| 6,287,325 B1 | 9/2001 | Bonutti |
| 6,299,448 B1 | 10/2001 | Zdrahala et al. |
| 6,328,758 B1 | 12/2001 | Tornier et al. |
| 6,334,446 B1 | 1/2002 | Beyar |
| 6,387,041 B1 | 5/2002 | Harari et al. |
| 6,406,480 B1 | 6/2002 | Beyar et al. |
| 6,447,524 B1 | 9/2002 | Knodel et al. |
| 6,451,024 B1 | 9/2002 | Thompson et al. |
| 6,527,774 B2 | 3/2003 | Lieberman |
| 6,544,273 B1 | 4/2003 | Harari et al. |
| 6,585,730 B1 | 7/2003 | Foerster |
| 6,635,058 B2 | 10/2003 | Beyar et al. |
| 6,656,183 B2 | 12/2003 | Colleran et al. |
| 6,663,642 B2 | 12/2003 | Beyar et al. |
| 6,692,516 B2 | 2/2004 | West, Jr. et al. |
| 6,730,110 B1 | 5/2004 | Harari et al. |
| 6,746,455 B2 | 6/2004 | Beyar et al. |
| 6,770,076 B2 | 8/2004 | Foerster |
| 6,773,437 B2 | 8/2004 | Ogilvie et al. |
| 6,855,157 B2 | 2/2005 | Foerster |
| 6,960,160 B2 | 11/2005 | Browning |
| 6,986,781 B2 | 1/2006 | Smith |
| 7,083,638 B2 | 8/2006 | Foerster |
| 7,090,690 B2 | 8/2006 | Foerster et al. |
| 7,309,337 B2 | 12/2007 | Colleran et al. |
| 7,744,613 B2 | 6/2010 | Ewers et al. |
| 7,938,847 B2 | 5/2011 | Fanton et al. |
| 8,100,940 B2 | 1/2012 | Leung et al. |
| 8,118,835 B2 | 2/2012 | Weisel et al. |
| 8,292,932 B2 | 10/2012 | Matthis et al. |
| 8,721,650 B2 | 5/2014 | Fanton et al. |
| 8,758,406 B2 | 6/2014 | Fanton et al. |
| 9,445,805 B2 | 9/2016 | Snell et al. |
| 9,539,001 B2 | 1/2017 | Fanton et al. |
| 2001/0051816 A1 | 12/2001 | Enzerink et al. |
| 2002/0082622 A1 | 6/2002 | Kane |
| 2002/0111653 A1 | 8/2002 | Foerster |
| 2003/0078465 A1 | 4/2003 | Pai et al. |
| 2003/0088272 A1 | 5/2003 | Smith |
| 2003/0120309 A1 | 6/2003 | Colleran et al. |
| 2004/0078054 A1 | 4/2004 | Biggs et al. |
| 2004/0098050 A1 | 5/2004 | Foerster et al. |
| 2004/0220617 A1 | 11/2004 | Pedlick et al. |
| 2004/0236170 A1 | 11/2004 | Kim |
| 2004/0260317 A1 | 12/2004 | Bloom et al. |
| 2004/0267275 A1 | 12/2004 | Cournoyer et al. |
| 2005/0080454 A1 | 4/2005 | Drews et al. |
| 2005/0187555 A1 | 8/2005 | Biedermann et al. |
| 2005/0245932 A1 | 11/2005 | Fanton et al. |
| 2006/0036244 A1 | 2/2006 | Spitler et al. |
| 2006/0089525 A1 | 4/2006 | Mamo et al. |
| 2006/0100630 A1 | 5/2006 | West, Jr. |
| 2006/0106422 A1 | 5/2006 | Del Rio et al. |
| 2006/0282081 A1 | 12/2006 | Fanton et al. |
| 2006/0282082 A1 | 12/2006 | Fanton et al. |
| 2006/0282083 A1 | 12/2006 | Fanton et al. |
| 2007/0156149 A1 | 7/2007 | Fanton et al. |
| 2007/0156150 A1 | 7/2007 | Fanton et al. |
| 2007/0156176 A1 | 7/2007 | Fanton et al. |
| 2007/0255317 A1 | 11/2007 | Fanton et al. |
| 2010/0292732 A1* | 11/2010 | Hirotsuka .......... A61B 17/0401 606/232 |
| 2011/0264141 A1 | 10/2011 | Denham et al. |
| 2011/0313453 A1* | 12/2011 | Krumme ............ A61B 17/0401 606/232 |
| 2012/0290004 A1 | 11/2012 | Lombardo et al. |
| 2015/0182213 A1* | 7/2015 | Gelfand ............. A61B 17/0401 606/232 |
| 2016/0296224 A1 | 10/2016 | Snell et al. |

FOREIGN PATENT DOCUMENTS

| | | |
|---|---|---|
| EP | 0 838 197 | 4/1998 |
| EP | 1 820 462 | 8/2007 |
| FR | 2 731 610 | 9/1996 |
| FR | 2 736 254 | 1/1997 |
| JP | H09 75374 | 3/1997 |
| WO | WO 94/28799 | 12/1994 |
| WO | WO 96/39948 | 12/1996 |
| WO | WO 97/30649 | 8/1997 |

(56) References Cited

FOREIGN PATENT DOCUMENTS

| | | |
|---|---|---|
| WO | WO 98/010693 | 3/1998 |
| WO | WO 98/11829 | 3/1998 |
| WO | WO 99/22648 | 5/1999 |
| WO | WO 00/035355 | 6/2000 |
| WO | WO 01/054586 | 8/2001 |
| WO | WO 2005/074827 | 8/2005 |
| WO | WO 2005/102190 | 11/2005 |
| WO | WO 2005/122954 | 12/2005 |
| WO | WO 2006/037131 | 4/2006 |
| WO | WO 2007/140309 | 12/2007 |
| WO | WO 2008/109087 | 9/2008 |
| WO | WO 2014/031578 | 2/2014 |

\* cited by examiner

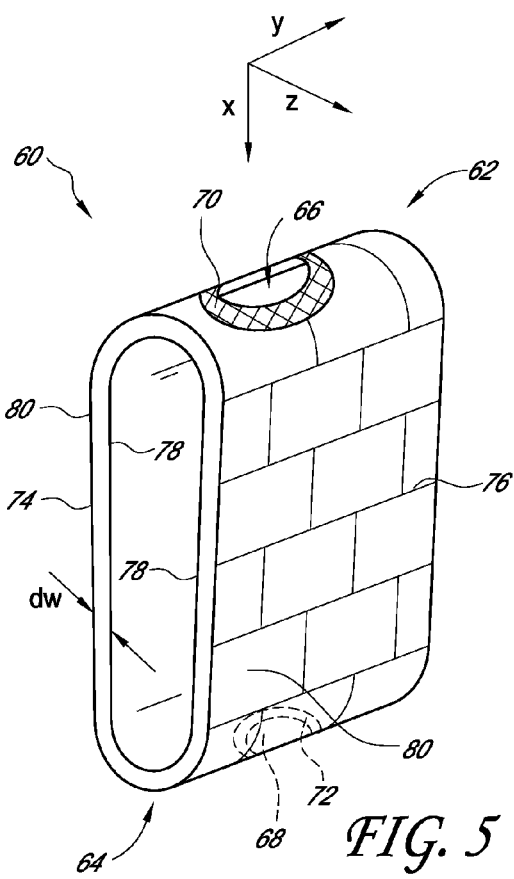
FIG. 5
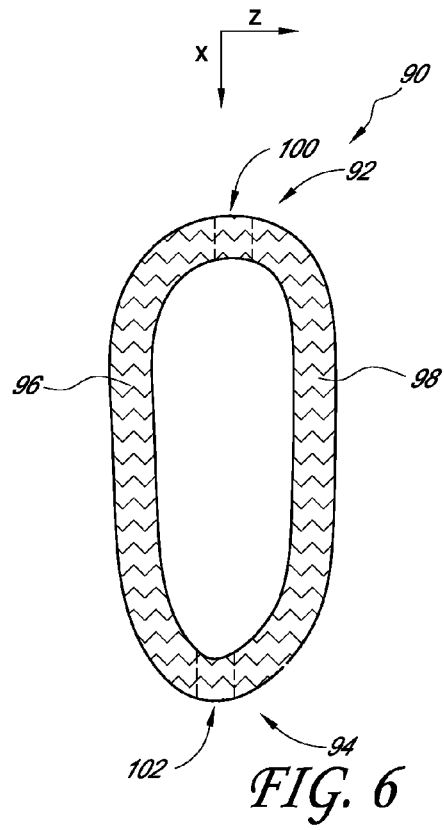
FIG. 6
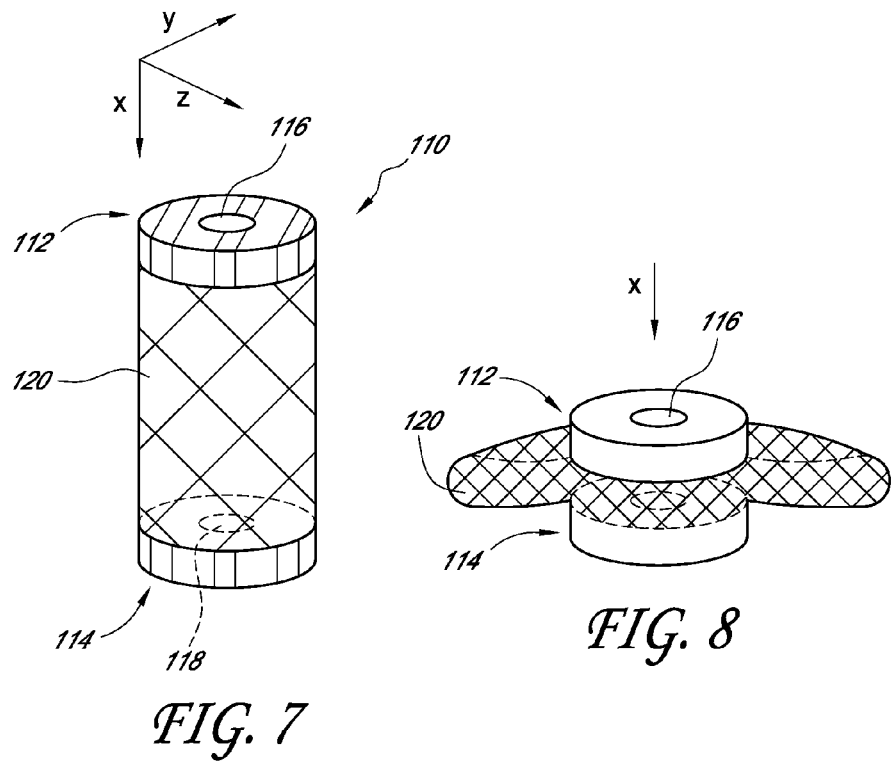
FIG. 7
FIG. 8

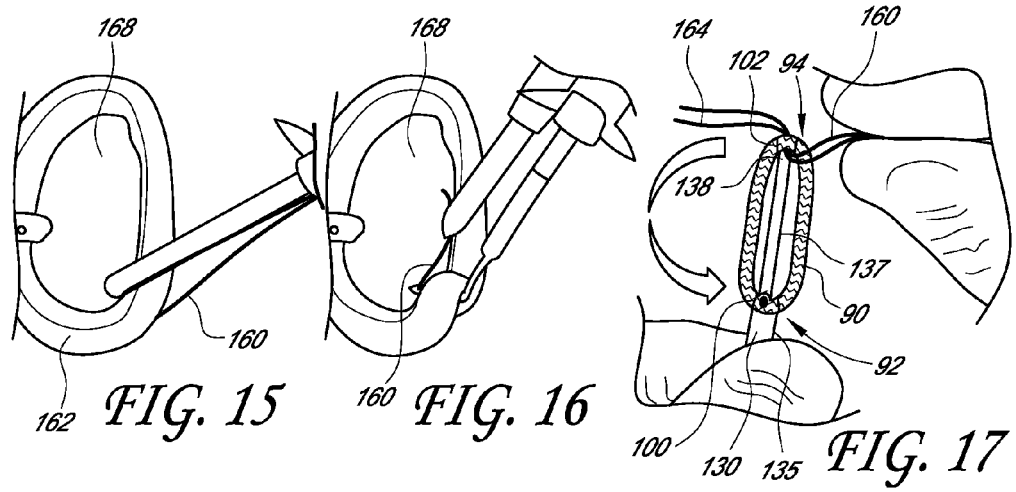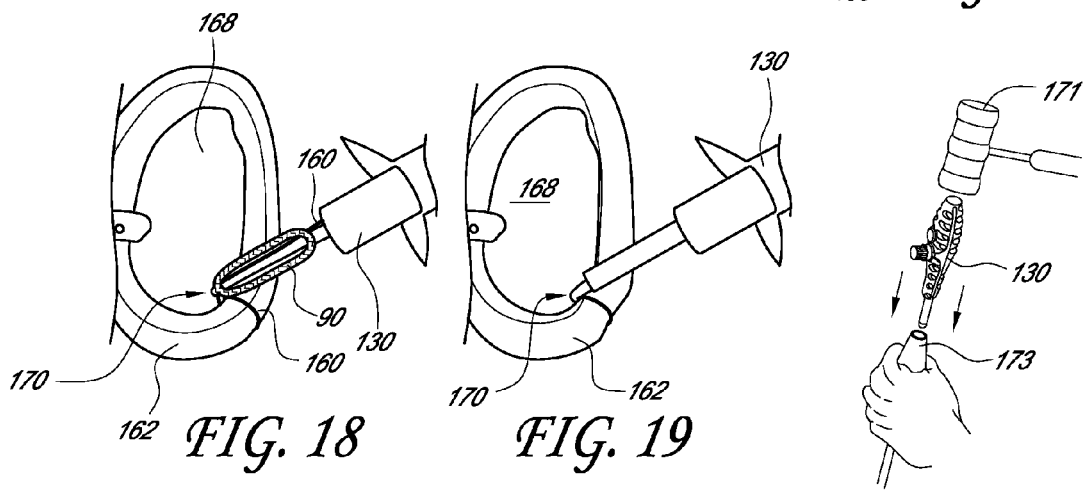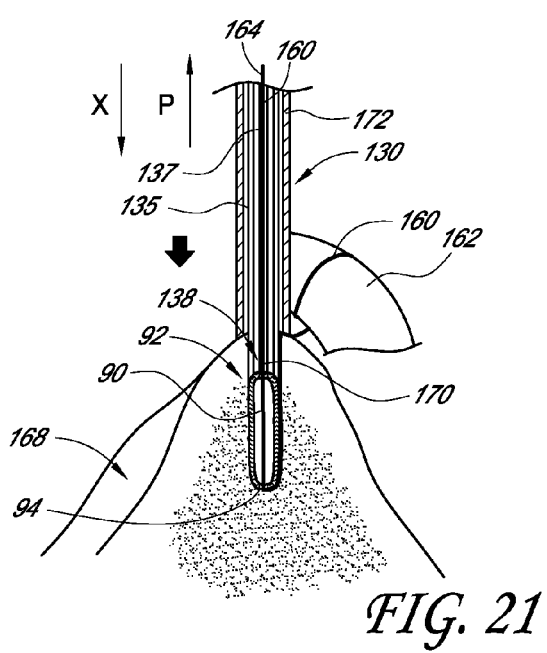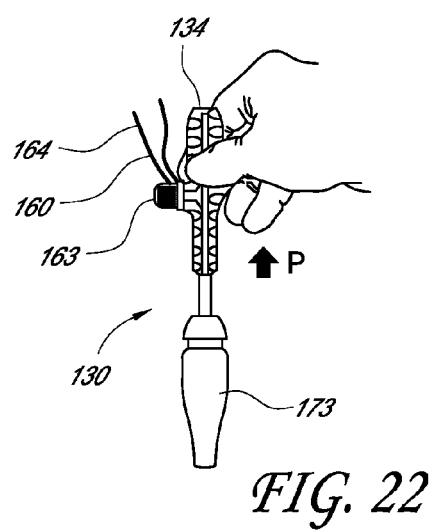

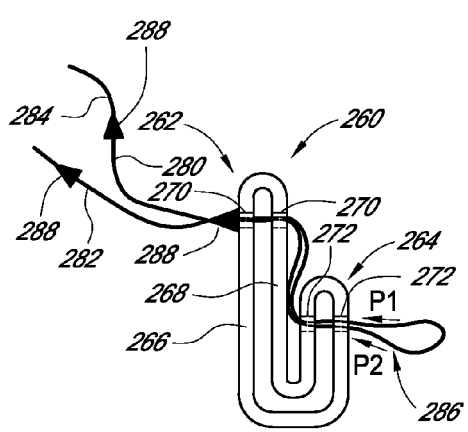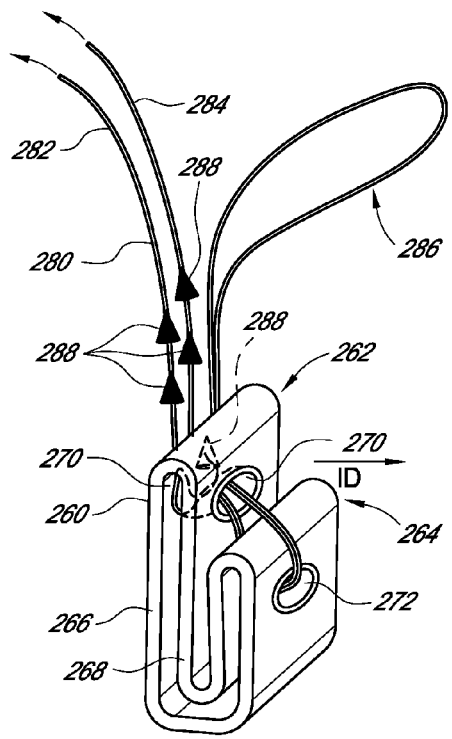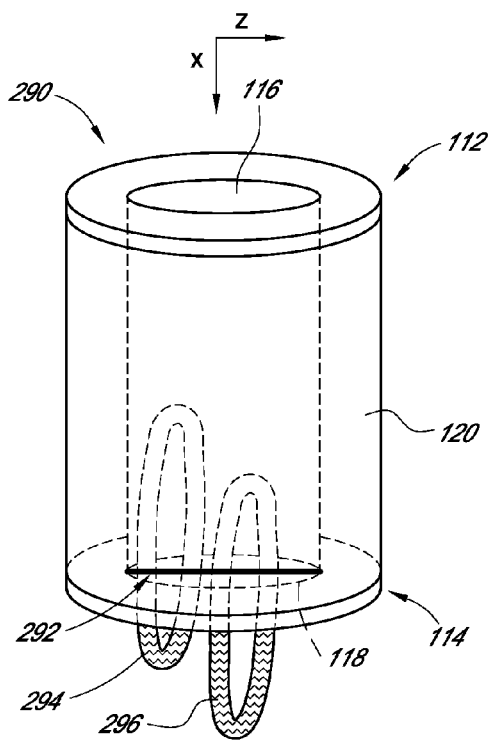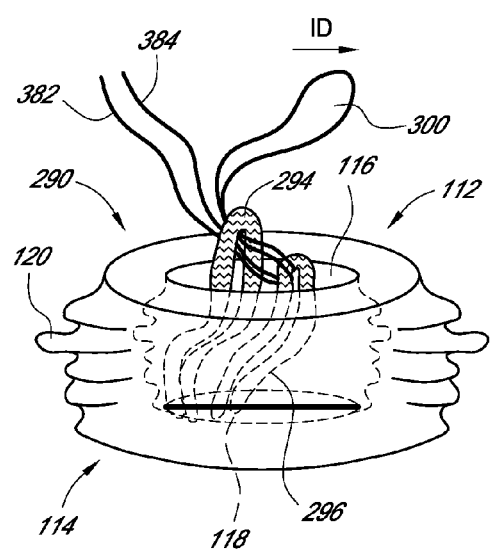
FIG. 28
FIG. 29
FIG. 30
FIG. 31

SUTURE FOR CONNECTING A HUMAN OR ANIMAL TISSUE, SOFT ANCHOR AND METHOD FOR ATTACHING A TISSUE TO A BONE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present application relates to sutures and soft anchors, and methods for attaching a tissue to a bone. The present application also relates to sutures for connecting a human or animal tissue to a bone, and soft anchors cooperating with the sutures.

Description of the Related Art

Tears of a soft tissue, for example ligaments or muscles, may be repaired by fixing them to a bone. For example, a torn labrum may be attached again to a glenoid. Various techniques are known, for example the usage of rigid, non-flexible anchors for a suture or flexible anchors for a suture. The ligaments or muscles are fixed using the suture and the anchor provided in the bone. For example, two suture tails are provided around the tissue and a knot is provided to tie the two suture tails together.

SUMMARY OF THE INVENTION

According to one aspect, embodiments relate to a suture for connecting a human or animal tissue comprising a suture strand, wherein at least two protrusions are provided on the suture strand, the protrusions are provided spaced apart from each other along the suture strand.

In an embodiment, the protrusions are unidirectional locking devices. The unidirectional locking devices have a first end in a passing direction, the suture having at the first end a first diameter corresponding substantially to the diameter of the suture strand, and a second end in a locking direction, the second end protruding in a radial direction from the circumference of the suture strand and having a locking surface. For example, at the second end, the suture has a second diameter being larger than the first diameter at the first end, so that the suture may pass through an opening having a diameter between the first diameter and the second diameter, but may lock when being moved in the locking direction. In other embodiments, the second end of the unidirectional locking devices may protrude from the suture strand, and/or may be collapsible to pass through an opening having substantially the same diameter than the suture strand. In such cases, the collapsible unidirectional locking devices may be biased or stressed in a radial direction of the suture strand.

In an embodiment, which may be combined with other embodiments, the protrusions are braided and/or woven. For example, they may be created during manufacture of the suture.

According to a further aspect, embodiments relate to a soft anchor, the soft anchor having a proximal end and a distal end in an insertion direction. At the proximal end and the distal end the soft anchor includes respectively at least one opening for a suture. In an embodiment, the opening(s) is(are) provided such that, in the first state, a suture may pass through the opening(s) in the insertion direction. In another embodiment, which may be combined with other embodiments disclosed herein, the opening(s) at the proximal and distal ends are provided such that, in the first state, the suture may pass through the opening(s) in a direction orthogonal to the insertion direction.

The proximal end and the distal end of the soft anchor are connected with at least one, in particular two, connecting portions. The soft anchor has a first state, in which it is adapted to be inserted into a bore in the insertion direction, and a second state, in which it may be locked in a bore. In the first state, the distal end and the proximal end define the extension of the soft anchor in insertion direction.

For example, in an embodiment, in the first state the extension of the soft anchor in an insertion direction is at least two times, in particular three times the extension of the soft anchor in a second direction extending in a plane orthogonal to the insertion direction.

In an embodiment, in the second state, the proximal end and the distal end have approached each other with respect to their distance in the first state. For example, the proximal end and the distal end may have in the second state a distance in insertion direction, which is less than one half of the distance between them in the first state in insertion direction, for example less than a third or a quarter of the distance between them in the first state. In an embodiment, in the second state the proximal end and the distal end are close to each other or may even contact each other.

In an embodiment, when changing from the first state to the second state, the at least one connecting portion may be pushed in the second direction and/or opposite to the second direction. In the second state, the soft anchor may have a larger extension in the second direction that in the first state.

In an embodiment, the connecting portion may be a wall. For example, the soft anchor may have one or two, in particular parallel, connecting portions, such that, in the first state in a cross-section being in a plane of the insertion direction and the second direction, the soft anchor has a ring shaped form, in particular a closed ring shaped form.

The soft anchor is, in an embodiment, woven from a suture, for example a biocomposite and/or absorbable suture.

In an embodiment, the opening(s) at the proximal and/or the distal ends are provided to have a diameter being smaller than the second diameter of the suture according to embodiment disclosed herein. For example, the diameter may greater than the first diameter of the suture according to embodiments disclosed herein.

The at least one opening at the proximal end and/or the at least one opening at the distal end are provided for the suture for fixing the tissue and have reinforced borders. For example a reinforcement braid may be used for that purpose.

According to another aspect, embodiments relate to a set of parts comprising a suture according to embodiments disclosed herein and a soft anchor according to embodiments disclosed herein, wherein the diameter of the opening(s) at the proximal and/or the distal end are provided to have a diameter being smaller than the second diameter of the suture.

According to a further aspect, the disclosure relates to a method for attaching a tissue to a bone, comprising: providing a suture comprising a suture strand, wherein at least two protrusions are provided on the suture strand, the protrusions are provided spaced apart from each other along the suture strand; providing a soft anchor having a proximal end and a distal end in an insertion direction, the proximal end and the distal end the soft anchor including respectively at least one opening for the suture, wherein the proximal end and the distal end of the soft anchor are connected with at least one, in particular two, connecting portions; passing the suture through the opening at the distal and then through the opening at the proximal end; inserting the soft anchor starting with its distal end into a bore in a bone; and pulling the suture further through the hole in opposite direction to the insertion direction while retaining the proximal end of the soft anchor in the same position.

For example, in the present method, the soft anchor may be according to an embodiment disclosed herein and/or the suture may be according to an embodiment disclosed herein.

In an embodiment, the suture comprises unidirectional locking devices and is inserted in the passing direction into the soft anchor, so that the passing direction is in opposite direction to the insertion direction.

For example, in an embodiment, during pulling the suture, when the soft anchor is in a bore, the soft anchor may deploy from first state to the second state.

In some embodiments, a method for securing a suture to a bone is provided. The method can include inserting a soft anchor into a bore in the bone. The method can include pulling a suture through at least one opening in the soft anchor. The suture can include a suture strand and at least two protrusions spaced apart from each other along the suture strand. Pulling of the suture through the at least one opening can cause the soft anchor to deploy from a first state in which the soft anchor is adapted to be inserted into the bore to a second state in which the soft anchor is locked in the bore. The soft anchor can be inserted into the bore in the bone in an insertion direction, and the suture can be pulled through at least one opening in the soft anchor in an opposite direction to the insertion direction. The soft anchor can have a proximal end and a distal end, wherein a proximal opening is positioned at the proximal end and a distal opening is positioned at the distal end, and the suture can be pulled through both the proximal and distal openings. The soft anchor can be inserted starting with its distal end into the bore in the bone. The proximal end of the soft anchor can be retained in the same position when the suture is pulled through the proximal and distal openings. The proximal end and the distal end of the soft anchor can approach each other when transitioning from the first state to the second state. The at least two protrusions can comprise unidirectional locking devices. The method can include passing the suture around a piece of soft tissue prior to pulling the suture through the at least one opening. The method can include pulling two portions of suture through the at least one opening. The two portions of suture can be two portions of the same suture comprising two groups of unidirectional locking devices directed in opposite directions. The soft anchor can be inserted into a bore in the glenoid. The direction of inserting the soft anchor can be opposite the direction of pulling the suture. The method can include the step of decreasing in size a loop configured to surround a tissue with the passage of each protrusion through the soft anchor. The method wherein the step of deploying to a second state causes the soft anchor to extend in a plane orthogonal to the direction of inserting the soft anchor. The method can include the step of attaching the suture to a torn labrum (or other tissue) to repair the torn labrum (or tissue).

In some embodiments, a suture fixation system is provided. The system can include a suture comprising a suture strand and at least two protrusions provided on the suture strand. The protrusions can be spaced apart from each other along the suture strand. The system can include a soft anchor. The soft anchor can include a proximal end and a distal end and a connecting portion extending therebetween. The soft anchor can include at least one opening disposed at the proximal end, the distal end, or both the proximal and distal ends. The suture can be configured to pass through the at least one opening in the soft anchor to cause the soft anchor to deploy from a first insertion state to a second locking state. The at least two protrusions can comprise unidirectional locking devices. The at least two protrusions can include a first group of unidirectional locking devices oriented in a first direction and a second group of unidirectional locking devices oriented in a second direction opposite the first direction. The at least two protrusions can have a braided geometry and can be integrated into the strand. The soft anchor can be ring shaped. The soft anchor can be weaved from a suture. The soft anchor can have an opening at the proximal end and an opening at the distal end, and the suture can be configured to pass through both openings to cause the openings to approach each other to deploy the soft anchor from the first insertion state to the second locking state. The system can include an insertion device configured to deliver the soft anchor into a bone and configured to pull the suture through the at least one opening in the soft anchor. The geometry of the suture can cause the soft anchor to deploy into the second locking state. The suture can includes two sections, including a first section of protrusions having a first passing direction and a second section of protrusions having a second passing direction. The first passing direction can be opposite the second passing direction. The first section and the second section can pass through the soft anchor to deploy the soft anchor to the second locking state.

In some embodiments, a suture fixation system is provided. The system can include a suture. The system can include a soft anchor comprising a proximal end comprising an opening, a distal end comprising an opening and a connecting portion extending therebetween. The system can include a bar traversing diametrically at least one of the openings. The system can include a first locking element and second locking elements disposed around the bar. The suture can be configured to pass through the first locking element, around the second locking element, and through the first locking element to cause the soft anchor to deploy from a first insertion state to a second locking state.

In some embodiments, a suture for connecting a human or animal tissue is provided. The suture includes a suture strand and at least two protrusions provided on the suture strand. In some embodiments, the protrusions are spaced apart from each other along the suture strand. The protrusions may comprise unidirectional locking devices. The protrusions may have a fixed relationship to the suture strand and comprise a leading edge having a first dimension transverse to the strand and a trailing edge with a second dimension transverse to the strand, the first dimension being less than the second dimension. The protrusions may be collapsible such that the distance that the protrusions extend from the suture strand is greater in a locking configuration and is less in a passing configuration. The protrusions may be braided or woven.

In some embodiments, a soft anchor is provided. The soft anchor includes a proximal end a distal end, and a connecting portion extending therebetween. The anchor can be disposed such that the distal end is inserted along an insertion direction prior to the proximal end. The anchor can include an opening disposed at the proximal end, the distal end, or both the proximal and distal ends. The opening can be configured to receive a suture. The openings can include a reinforcement braid. The dimension of the anchor in a direction orthogonal to the insertion direction is 5 to 10 times the thickness of a wall of the anchor. The openings can be configured to receive a suture in the insertion direction. The openings can be configured to receive a suture in a direction orthogonal to the insertion direction.

The connecting portion can comprises a first body extending between the proximal end and the distal end and a second body extending between the proximal end and the distal end, the first and second bodies being disposed laterally of an axis intersecting the proximal and distal ends of the soft anchor. The first and second bodies can comprise walls that extend along each other in the insertion direction and that are coupled at the proximal and distal ends such that the soft anchor comprises a closed ring. The soft anchor can comprises a first configuration for insertion in which a length comprising the distance from the proximal end to the distal end along a first axis intersecting the proximal end and the distal end is greater than a width comprising the distance between lateral edges of the soft anchor along a second axis perpendicular to the first axis. The length can be at least two times the width. The length can be three times the width. The soft anchor comprises a second configuration for insertion in which a length comprising the distance from the proximal end to the distal end along a first axis intersecting the proximal end and the distal end, the length in the second configuration being less than the length in the first configuration. The length of the soft anchor in the second configuration can be no more than ⅓ the length of the soft anchor in the first configuration. The length of the soft anchor in the second configuration can be no more than ¼ the length of the soft anchor in the first configuration. The proximal end and the distal end can be in contact with each other in the second configuration. The soft anchor can comprises a second configuration for insertion in which a width comprising the distance between lateral edges of the soft anchor along a second axis perpendicular to the first axis that is greater than the width in the first configuration.

BRIEF DESCRIPTION OF THE DRAWINGS

So the manner in which the above-recited features of the present inventions can be understood in detail, more particular description of the inventions, briefly summarized above, may be made by referenced embodiments. The accompanying drawings relate embodiments of the invention and are described in the following:

FIG. 5 shows schematically a soft anchor according to an embodiment;

FIG. 6 shows schematically another embodiment of a soft anchor;

FIG. 7 shows schematically a further embodiment of a soft anchor in a first state;

FIG. 8 shows schematically the soft anchor of FIG. 7 in a second, deployed state;

FIGS. 15 to 26 show the different steps of a method for attaching a soft tissue to a bone according to an embodiment;

FIGS. 28 and 29 show schematically another embodiment of a soft anchor with a respective suture in a cinched configuration; and FIGS. 30 and 31 show schematically a further embodiment of a soft anchor in a first and second state with a respective suture in a cinched configuration.

DETAILED DESCRIPTION OF THE PREFERRED EMBODIMENT

Reference will now be made in detail to various embodiments, one or more examples of which are illustrated in the figures. Each example is provided by way of explanation, and is not meant as a limitation of the invention. Within the following description of the drawings, the same reference numbers refer to the same components. Generally, only the differences with respect to the individual embodiments are described.

Figure 1:
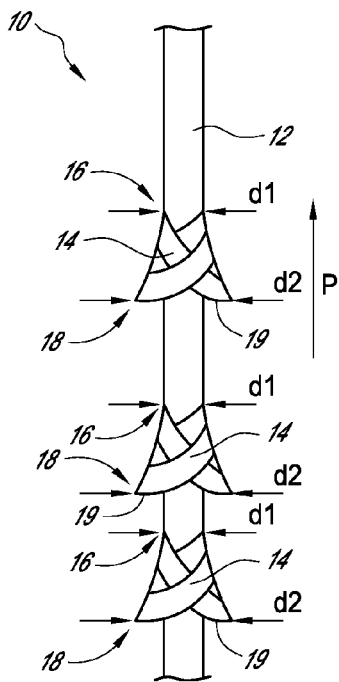
FIG. 1 shows schematically a suture for connecting human or animal tissue according to an embodiment.

FIG. 1 shows schematically a suture 10 for connecting human or animal tissue. The suture includes a suture strand 12. According to an embodiment, which may be combined with other embodiments disclosed therein, a plurality of protrusions, for example unidirectional locking devices 14, are provided on the suture strand 12. The unidirectional locking devices 14 may be provided regularly, for example equidistantly, on the suture strand 12. The unidirectional locking devices 14 of the suture 10 may have a substantially conical shaped geometry. According to an embodiment, the unidirectional locking devices 14 have a braided geometry and are integrated into the suture strand 12. Thus, according to an embodiment, the suture 10 has a barbed appearance.

The unidirectional locking devices 14 have, according to an embodiment, which may be combined with other embodiments disclosed herein, a first end 16 in a passing direction P and a second end 18 in a locking direction being in opposite direction to the passing direction P. The passing direction P is the direction that the suture is moved in relation to another structure, such as an opening in a tissue or anchor. The suture 10 has at the first end 16 of the unidirectional locking device 14 a first diameter d1, which has substantially the same diameter as the suture strand 12. The suture 10 has at the second end 18 of the unidirectional locking device 14 a second diameter d2 which is larger than the first diameter d1. At the second end 18, the unidirectional locking device 14 is provided with a locking surface 19 directed substantially to the locking direction. In some embodiments, the transition from the first diameter d1 to the second diameter d2 is substantially conical.

The conical geometry makes the suture 10 unidirectional, so that it may pass in the passing direction P through an opening having a diameter corresponding substantially to the diameter of the suture strand 12 (e.g., equal to or larger) and having a lower (e.g., smaller) diameter than the second diameter d2. As discussed further below, the opening can be disposed in a soft anchor or the wall of another structure.

The unidirectional locking devices 14 are compressible to allow them to pass through the opening having a diameter smaller than the second diameter d2. Upon passing through the opening, the unidirectional locking devices 14 return to their original, uncompressed state. However, the suture 10 is locked, when it is pulled in the locking direction (opposite to the direction P), as a locking surface 19 of one of the unidirectional locking devices 14 would abut against the wall having or defining the opening. The locking surface 19 prevents the unidirectional locking device 14 of the suture 10 from moving in the locking direction through the opening when the suture 10 is pulled or tensioned in the locking direction.

Figure 2:
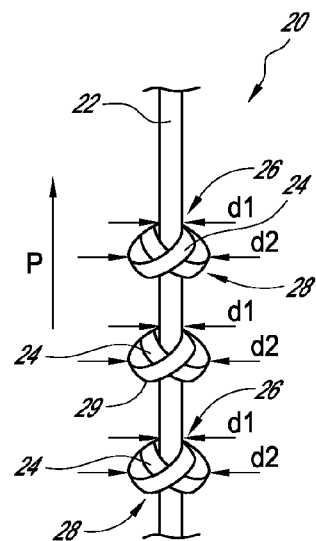
FIG. 2 shows schematically another embodiment of a suture for connecting human or animal tissue.

FIG. 2 shows another embodiment of a suture 20. The same features are designated with the same reference numbers as in FIG. 1 increased by 10. The suture 20 for connecting human or animal tissue includes a suture strand 22 on which a plurality of protrusions, for example unidirectional locking devices 24, are provided. The unidirectional locking devices 24 have a first end 26 in a passing direction P and a second end 28 in a locking direction being in opposite direction to the passing direction P. The suture 20 has at the first end 26 of the unidirectional locking device 24 a first diameter d1, which has substantially the same diameter as the suture strand 22. The suture 20 has at the second end 28 of the unidirectional locking device 24 a second diameter d2 which is larger than the first diameter d1. At the second end 28, the unidirectional locking device 24 is provided with a locking surface 29. The unidirectional locking devices 24 differ from the unidirectional locking devices 14 of FIG. 1 in their geometry. In some embodiments, the transition from the first diameter d1 to the second diameter d2 is substantially curved. For example, the unidirectional locking devices 24 have a more spherical or knotted geometry (e.g., a curved transition from d1 to d2). However, the function is identical to the unidirectional locking devices 14 of FIG. 1. As in the embodiment of FIG. 1, the unidirectional locking devices should assure that the suture 20 only passes in the passing direction P through an opening of an anchor, which will be explained further below.

Figure 3:
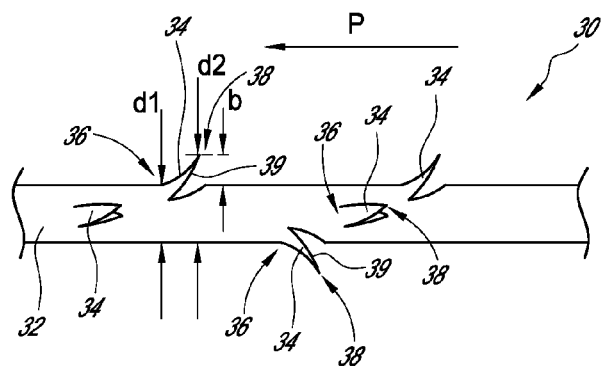
FIG. 3 shows a schematically further embodiment of a suture for connecting human or animal tissue.

FIG. 3 shows a further embodiment of a suture 30 having a plurality of protrusions forming unidirectional locking devices 34. The same features are designated with the same reference numbers as in FIG. 1 increased by 20.

The unidirectional locking devices 34 are arrow shaped and have a semi-collapsible end. In particular, the unidirectional locking devices 34 have a first end 36 in a passing direction P and a second end 38 in a locking direction, wherein at the first end 36 the suture 30 has approximately the first diameter d1 of the suture strand 32. The second end 38 protrudes from the suture strand 32 so that the suture 30 has at the second end 38 a width of d2 which is greater than d1 based on the number of unidirectional locking devices at a specific point of the suture, and the distance b between the second ends 38 and the perimeter of the suture strand 32. For example, if two locking devices are disposed at the specific point and are on opposite sides of the suture, the width of the suture will be d1+2×b. The distance b is the distance the second end 38 protrudes from the perimeter of the suture strand 32. At the second end 38, the unidirectional locking device 34 is provided with a locking surface 39. When cooperating with an opening having a diameter between the first diameter d1 of the suture 30 and second diameter d2 (e.g., a diameter greater than d1 and less than d2), the suture 30 may only pass in the passing direction P through said opening. In some embodiments, the transition from the first diameter d1 to the second diameter d2 is substantially curved, wedged or arrow-shaped. The unidirectional locking devices 34 have a semi-collapsible, second end 38, so that they form a barbed structure.

In other embodiments, which may be combined with the embodiment disclosed herein, other geometries may be used to provide the unidirectional locking device, so that a barbed or locking effect is created like in the embodiments of FIGS. 1 to 3.

In further embodiments, the protrusions, e.g., unidirectional locking devices, provided on the suture strand may have a diamond-shaped geometry. In contrast to the conical shaped geometry, which is unidirectional and explained with respect to FIG. 1, the diamond-shaped geometry of the protrusions may be used to allow for multi-directional suture passing through an opening, when being pulled with a certain force.

In some embodiments, different types and geometries of protrusions may be combined on a suture (e.g., unidirectional locking devices, multi-directional locking devices). In other embodiments, the number and spacing of the protrusions may vary.

In an embodiment, the protrusions, e.g., unidirectional locking devices, are formed, in particular, braided and/or knotted, during the weaving process of the suture strand or after the sutures are woven or otherwise manufactured. For example they are integrated into the suture strand. Thus, they may be made of the same material as the suture strand. In other embodiments, the unidirectional locking devices or other protrusions may be also over-molded, for example injection molded onto a suture strand. The molded protrusions may be molded of a PEEK (polyether ether ketone) or other bioabsorbable materials, for example P4HB (Poly-4-hydroxybutyrate) or PLA (Poly lactic acid) or a combination thereof, or other materials, for example bioabsorbable p4hb 5Poly-4-hydroxybutyrate) or bioabsorbable PLA (Poly lactic acid) or a combination thereof.

In an embodiment, which may be combined with other embodiments herein, the suture, in particular the suture strand, may be produced on or from permanent or absorbable fiber. For example, a permanent fiber may be a polyethylene fiber. For example, an absorbable fiber may be fabricated from a resorbable polymer, for example P4HB (Poly-4-hydroxybutyrate) or PLA (Poly lactic acid), or a combination thereof.

Figure 4:
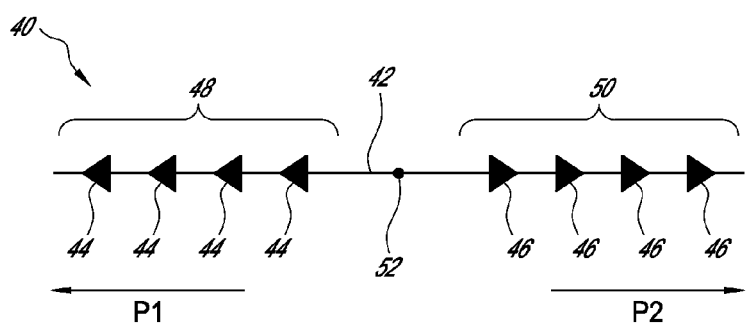
FIG. 4 shows schematically an arrangement of protrusions on a suture for connecting human or animal tissue according to an embodiment.

FIG. 4 shows schematically a further embodiment of a suture 40. The suture 40 includes a suture strand 42 on which a plurality of protrusions, for example, unidirectional locking devices 44, 46, are arranged. The unidirectional locking devices 44, 46 may be a unidirectional locking device according to an embodiment disclosed herein, for example one of the locking devices shown in FIGS. 1 to 3.

The suture 40 includes two adjacent sections, namely a first section 48 having a first passing direction P1 and a second section 50 having a second passing direction P2 being, along the suture, in an opposite direction to the first passing direction P1. The first passing direction P1 of the first section 48 is provided by a first group of unidirectional locking devices 44 and the second passing direction P2 is provided by a second group of unidirectional locking devices 46. The unidirectional locking devices of each group are arranged on a respective section 48, 50 of the suture strand 42. Both sections 48, 50 are arranged, such that the suture 42 has a point 52 from which the first and second passing directions P1, P2 move away. In some embodiments, the point 52 and the suture 42 near the point 52 form a loop around soft tissue, as shown in FIGS. 23-26.

FIGS. 5 to 8 show schematically different soft anchors.

FIG. 5 shows schematically an embodiment of a soft anchor 60 in a first state. The anchor 60 has a first state, in which the anchor 60 is adapted to be inserted into a bore in the insertion direction X, and a second state, in which it is locked in a bore. In the first state, the anchor 60 has an elongated form in the insertion direction X. In the insertion direction X, the anchor 60 has a proximal end 62 and distal end 64. In the first state, the distal end 64 and the proximal end 62 define the extension of the anchor 60 in the insertion direction X. At the proximal end 62 and the opposite distal end 64, the anchor comprises respectively at least one opening 66, 68 adapted for receiving a suture according to an embodiment disclosed herein. In other embodiments, the anchor 60 may comprise respectively two, three, or more openings at the proximal end 62 and/or the distal end 64 of the anchor 60.

In an embodiment, which may be combined with another embodiment disclosed herein, the borders of the openings 66, 68 are reinforced for better retaining the sutures, such as sutures comprising the unidirectional locking devices. For example, the openings can be reinforced by providing a reinforcement braid 70, 72 around the openings 66, 68. In some embodiments, the borders of the openings 66, 68 are reversibly stretchable larger, e.g., can stretched to a wider dimension then return toward a narrower dimension. In some embodiments, the protrusions, in particular the the unidirectional locking devices are reversibly compressible, for example as shown in the embodiment of FIGS. 1-3, in order for the protrusions to pass through the openings 66, 68 and subsequently lock, in case of the unidirectional locking devices, the suture to the anchor 60.

The proximal end 62 and the distal end 64 are connected by two walls 74, 76 forming connecting portions. In some embodiments, the two walls 74, 76 are flat walls. The walls 74, 76 are arranged substantially parallel in the first state of the anchor 60. In particular, the walls 74, 76 are spaced apart in a second direction Z being orthogonal to the insertion direction X. The walls 74, 76 extend in a plane defined by the insertion direction X and a third direction Y, the third direction Y being orthogonal to the insertion direction X and orthogonal to the second direction Z. For example, in an embodiment, the walls 74, 76 have a larger extension in the insertion direction X than into the third direction Y. For example, the extension of the walls 74, 76 in the third direction Y is at least 5 times the thickness dw of the wall, in particular at least 10 times dw. The anchor 60 has into the third direction Y a larger extension than into the second direction Z, so that the anchor 60 has a flat body in the first state.

In some embodiments, the anchor 60 has a ring shaped geometry in a plane defined by the insertion direction X and the second direction Z. For example, the extension into the insertion direction X is, in the first state, at least two times the extension into the second direction Z, for example about three to four times the extension into the second direction Z.

The anchor 60 can be collapsed from the first state shown in FIG. 5 to a second state (not shown) in a controlled way, such that walls 74, 76 connecting in parallel the proximal end 62 with the distal end 64 are pushed into opposite directions in the second direction Z. Thus, the extension in the second direction Z in the second state is larger than the extension in the second direction Z in the first state. In particular, the anchor 60 is forced into the second state by approaching the first opening 66 at the proximal end 62 toward the second opening 68 at the distal end 64. For example, the suture described with respect to FIGS. 1 to 4 may be used to transition the anchor 60 from the first state to the second state, as described herein.

According to an embodiment, which may be combined with other embodiments disclosed herein, the anchor 60 is knotless and can be woven from a suture. Thus, the anchor is not rigid, but is soft. In some embodiments, the soft anchor body is a single piece woven construction.

The suture for weaving the anchor body 60 may be a permanent or absorbable suture according to an embodiment, which may be combined with other embodiments herein. For example, a permanent suture may be a polyethylene suture, e.g. Ultra-high-molecular-weight polyethylene (UHMWPE). For example, an absorbable suture may be fabricated from a resorbable polymer, for example P4HB (Poly-4-hydroxybutyrate).

In an embodiment, a suture for connecting a tissue to a bone is passing through the openings 66, 68 at the proximal and distal ends 62, 64 and would be arranged in the space between the first wall 74 and the second wall 76.

In another embodiment, which may be combined with the embodiments disclosed herein, the walls 74, 76 connecting the proximal end 62 with the distal end 64 are hollow. In other words, the walls 74, 76 may comprise two layers, namely an inner layer 78 and an outer layer 80.

For example, in an embodiment, the openings 66, 68 at proximal end 62 and the distal end 64 are only provided in the outer layer 80. The outer layer 80 does not provide access to the space between the first wall 74 and the second wall 76. Thus, strands or sutures passing through the anchor 60 may pass through the walls 74, 76 between the inner layer 78 and the outer layer 80 before reaching the openings 66, 68 at the opposite end of the anchor 60. In other words, the ring shaped anchor body could be hollow on the inside turning it into a sheath that a suture, for example the suture with protrusions according to an embodiment disclosed herein, would pass through.

FIG. 6 shows another embodiment of a soft anchor 90. The soft anchor of FIG. 6 may comprise some of the features of the embodiment of FIG. 5, for example, the materials and the reinforcements at the border of the openings.

The anchor 90 has an elongated shape in inserting direction X in a first state shown in FIG. 6. The anchor 90 has a proximal end 92 and a distal end 94 which is connected in parallel by two connecting portions 96, 98. In the embodiment of FIG. 6, the anchor 90 is provided by a body having a round section forming a loop. The anchor body is woven according to an embodiment. At least one opening 100, 102 is provided respectively at the proximal end 92 and the distal end 94.

The extension of the connecting portions 96, 98 in a second direction Z being orthogonal to the insertion direction in X is substantially equal to the extension of the anchor in a third direction Y, the third direction Y being orthogonal to the insertion direction X and orthogonal to the second direction Z.

The anchor 60 of FIG. 6 is shown in the first state in which the extension in the insertion direction X is greater than the extension in the second direction Z. For example, in the present example, the extension in the insertion direction X is at least two times the extension in the second direction Z.

The second state of the anchor shown in FIG. 6 will be explained with respect to FIGS. 12 and 14 here below.

FIGS. 7 and 8 show a further embodiment of a soft anchor 110. FIG. 7 shows the anchor 110 in a first state and FIG. 8 shows the anchor 110 in a second, deployed state. The anchor 110 has an elongated shape in the insertion direction X in a first state shown in FIG. 7. In some embodiments, the elongated shape is substantially cylindrical.

The anchor 110 has a proximal end 112 and distal end 114. In some embodiments, the proximal end 112 and the distal end 114 are flat and substantially disc shaped. In the embodiment shown in FIGS. 7 and 8, the proximal end 112 and distal end 114 have surfaces with substantially circular perimeters. In other embodiments, the proximal and distal ends 112, 114 may have another form, for example they may have a perimeter with an oval, rectangular or have a polygonal form.

The proximal and the distal ends 112, 114 include respectively an opening 116, 118. In some embodiments, the proximal end 112 and/or the distal end 114 may include two, three, or more openings. A wall 120 connects the proximal end 112 with the distal end 114. In some embodiments, the extension of the wall 120 in a second direction Z being orthogonal to the insertion direction in X is substantially equal to the extension of the anchor in a third direction Y, the third direction Y being orthogonal to the insertion direction X and orthogonal to the second direction Z. The wall 120 can have a circular outer perimeter in the Y-Z plane.

In some embodiments, the anchor 110 has a cross-section that is substantial circular in a plane orthogonal to the insertion direction X. In other embodiments, where the proximal end 112 and the distal end 114 have another shape, for example if the ends 112, 114 are oval, rectangular, or in a polygonal form, the wall 120 forms a connector portion between the proximal end 112 and the distal end 114, and has also the respective form. In other words, in the first state, the anchor 110 forms an enclosed shaped, such as a hollow cylinder in the general meaning of cylinder and is not limited to a circular cylinder.

The anchor 110 may collapse into the second state, shown in FIG. 8, where the proximal end 112 and the distal end 114 are moved toward each other, and in some embodiments, may abut each other. The wall 120 is then pushed into a radial direction so that the diameter in the second direction Z and the third direction Y is substantially increased with respect to the first state.

For example, if the anchor 110 is inserted in the inserting direction X in the first state into a bore having a diameter corresponding to the diameter of the proximal end 112 or the distal end 114, and then subsequently manipulated to assume the form of the second state. As can be seen from FIG. 8, in the second state the diameter of the anchor 110 in a plane orthogonal to the insertion direction X, or a second direction Z orthogonal to the insertion direction X, has increased due to the wall 120 which has been pushed in several radial directions. Thus, the anchor 110 is not able to pass through the bore again. In other words, the anchor 110 is collapsed in FIG. 8 to prevent removal of the anchor 110 from the bore.

In the embodiment of FIGS. 7 and 8, a suture passing through the openings 116, 118 would go through the center of the enclosed space defined by the wall 120, which in some embodiments is generally tubular or cylindrical.

Other geometries could be used for the soft anchors. The shape of the body of the soft anchor according to embodiments of this invention allows for controlled collapse and superior pull-out strength, in particular when inserted into a bore.

In an embodiment, which may be combined with other embodiments disclosed herein, the soft anchors 60, 90, 110 may in the second state collapse in multiple axes, in other words, the walls may extend in a plane orthogonal to the insertion direction X in multiple directions.

Figure 9:
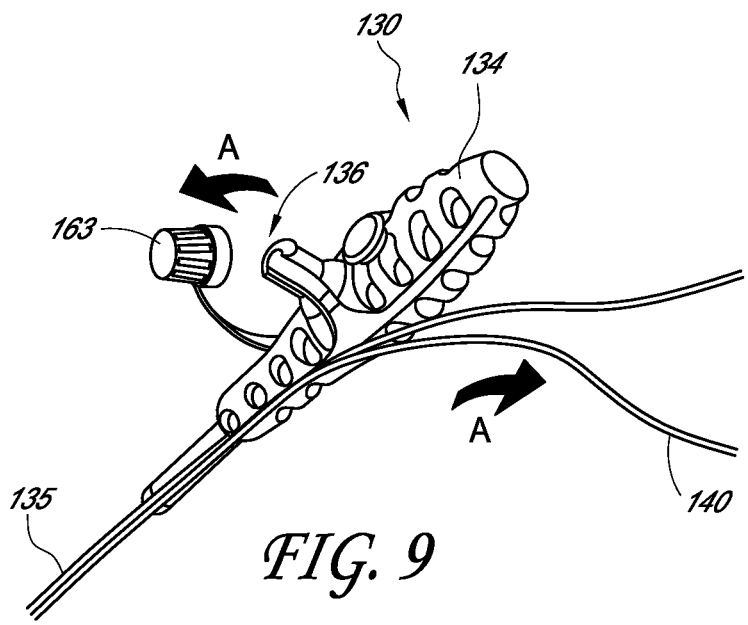
FIG. 9 shows schematically an upper or proximal portion of an inserter device for inserting the soft anchor.

FIG. 9 shows an insertion or inserter device 130 for usage with the soft anchors and the sutures according to embodiments disclosed herein. The insertion device 130 has a hollow tube 135 at its distal end through which at least one suture 140, for example two or more sutures may pass. The insertion device 130 includes a handle 134 at the proximal end for manipulating the insertion device 130. The handle 134 has an opening 136 through which the sutures 140 may pass to be able to be pulled, as indicated by the arrow A1, and a second passage orthogonal to the opening 136 through which the suture 140 may pass or be able to be pulled, as indicated by the arrow A2.

Figure 10:
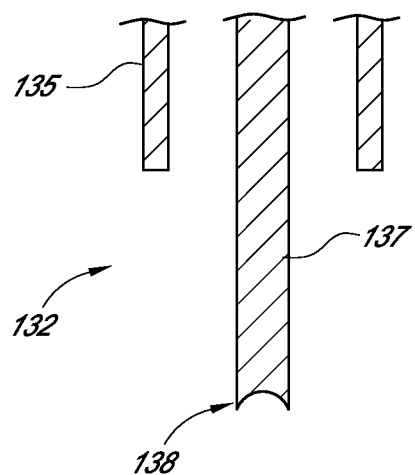
FIG. 10 shows schematically a cross section of a distal end of the inserter device of FIG. 9.

FIG. 10 shows the distal end 132 of the insertion device 130 in a simplified enlarged cross-sectional view. The distal end 132 comprises a cannulated tube 135 in which a shaft 137 is arranged. The shaft 137 can be solid and comprises a shaped portion 138 at its distal end for moving the distal end of a soft anchor into a bore of a bone. In some embodiments, the shaped portion can be forked, pointed or any other shape. The shaft 137 is independently movable in longitudinal direction of the insertion device 130 with respect to the tube 135. As shown in FIG. 9, one or more sutures 140, or the ends of the same suture, may be passed through the tube 135. The unidirectional locking devices of the sutures are oriented within the insertion device 130 so that movement in the direction A causes the unidirectional locking devices to pass through the anchors in passing direction P. The shaft 137 has two positions, namely an extended position, in which the shaft 137 extends out of the tube 135, and a retracted position, in which the shaft 137 and in particular the shaped portion 138 is retracted into the tube 135.

FIGS. 11 to 14 show how the suture 140 comprising the unidirectional locking devices 14 cooperates with a soft anchor according to an embodiment disclosed herein. The suture 140 has at the first end 146 of the unidirectional locking device 144 a first diameter d1, which has substantially the same diameter as the suture strand 142. The suture 140 has at the second end 148 of the unidirectional locking device 144 a second diameter d2 which is larger than the first diameter d1. At the second end 148, the unidirectional locking device 144 is provided with a locking surface 149. The unidirectional locking device 144 can have similar features to 14, 24, 34, 44, 46 of embodiments shown in FIGS. 1-4. FIGS. 11 to 14 show the usage of the anchor 90 according to FIG. 6. However, also other anchors, such as anchors 60, 110, according to embodiments disclosed herein may be used.

Figure 11:
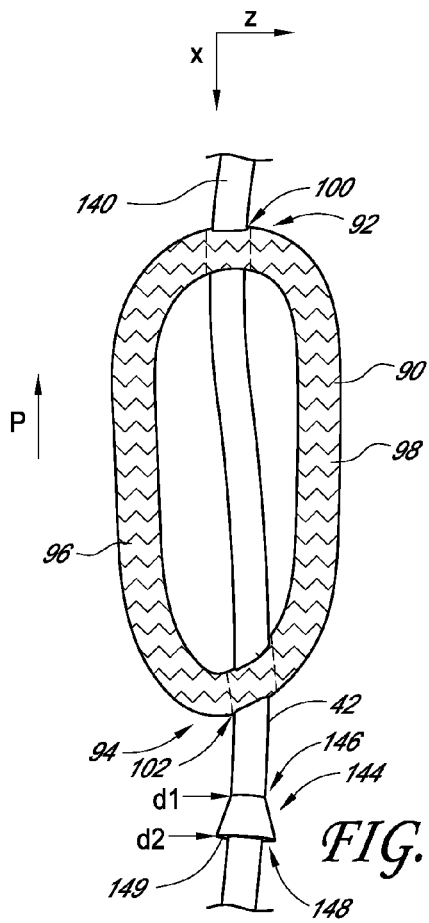
FIG. 11 shows schematically the soft anchor of FIG. 6 with a suture provided therethrough.
Figure 12:
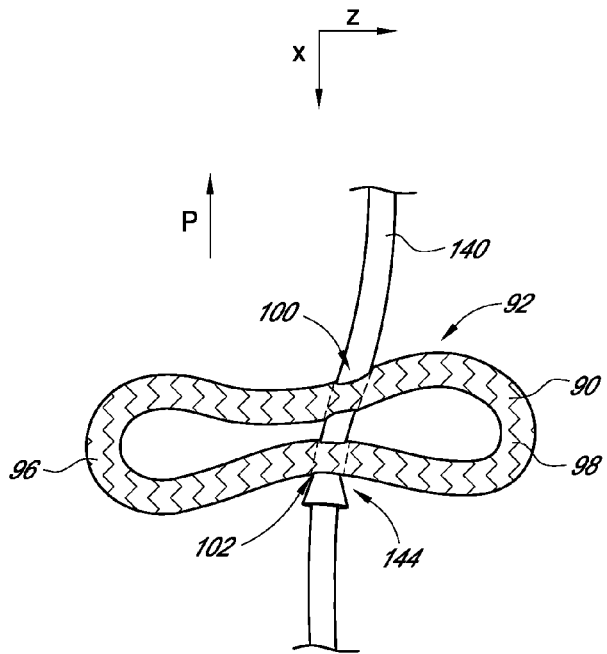
FIG. 12 shows the soft anchor of FIG. 11 in a deployed state.

In FIG. 11, the anchor 90 is in the first state and in FIG. 12, the anchor 90 is in the second state. In FIG. 11, the unidirectional locking device 144 on the suture 140 has not made an initial contact with the anchor 90. The suture 140 is passed through the openings 100, 102 at the proximal and distal end 92, 94 of the anchor 90 in the passing direction P. In some embodiments, the passing direction P is in opposite direction to the insertion direction X. The diameter of the openings 100, 102 is sized between the first diameter d1 and the second diameter d2 of the suture 140 (e.g., a diameter greater than d1 and less than d2), preferably close to the first diameter d1. Although FIGS. 11-14 illustrate a single suture 140 passing through the openings 100, 102 of the anchor 90, multiple sutures or portions of the same suture may also pass through the openings 100, 102. In some embodiments, the unidirectional locking devices of multiple sutures or portion of the same suture are oriented so that the passing direction P is the same for all sutures when passed through the openings 100, 102.

Figure 13:
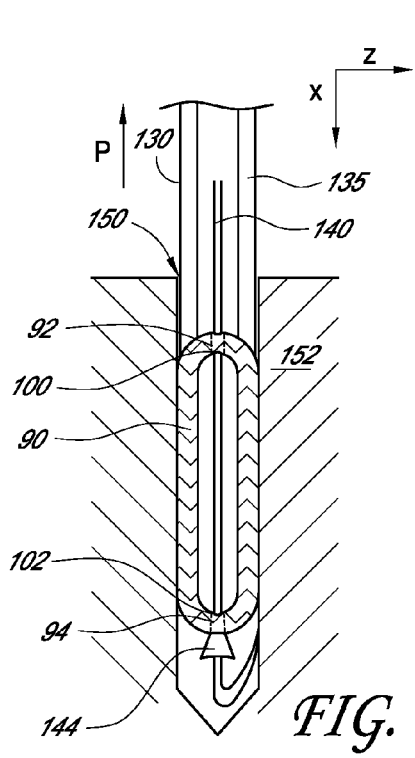
FIG. 13 shows schematically the soft anchor with the suture of FIG. 11 provided in a bore in a first state.

In some embodiments, the suture 140 or sutures may pass through the openings 100, 102 in the anchor 90 and pass through the tube 135 toward opening 136 of the insertion device 130, as shown in FIG. 9, to load the suture(s) 140 into the insertion device 130. In some embodiments, the anchor 90 is loaded into the insertion device 130 when the anchor 90 is in the first state. While the anchor is maintained in the first state, the anchor 90 with the suture 140 may be inserted into a bore 150 of a bone 152 as shown in FIG. 13. For example, with the suture 140 or sutures passing through the openings 100, 102 in the anchor 90, the anchor 90 may be inserted with the distal end 132 of the inserter device 130, shown in FIG. 10. The distal end 138 of the shaft 137 engages the anchor 90 such that the anchor 90 is pushed down to the distal end of the bore 150 in the insertion direction X. In some embodiments, the shaft 137 of the insertion device 130 engages the inner side of the distal end 94 of the anchor 90 (not shown). In some methods, the shaft 137 of the inserter device 130 is moved in proximal direction to retract the shaft 137 into the tube 135. The distal end of the tube 135 rests in contact with the proximal end 92 of the anchor 90, as shown in FIG. 13. In a step, the suture 140 is pulled in the passing direction P, so that a unidirectional locking device 144 engages or comes into contact with the distal end 94 of the anchor 90 (see for example FIG. 13). In FIG. 13, the unidirectional locking device 144 has not passed through openings 100, 102. Then, in a further step, the suture 140 is further pulled in the passing direction P, whereas the proximal end 92 of the soft anchor 90 is held in place, for example by the distal end of the tube 135 of the insertion device 130.

Upon further pulling of the suture 140 in the passing direction P, the connecting portions 96, 98 of the anchor 90 start to deploy in a plane orthogonal to the insertion direction X, for example in the second direction Z and/or in the third direction Y. In other words, the suture 140 is pulled and the unidirectional locking device 144 comes into contact with the distal end 94 of the anchor 90 and then begins to pull the distal end 94 of the anchor 90 up proximally. The unidirectional locking devices 144 will urge the anchor 90 in the passing direction P before passing through the opening 102. The unidirectional locking devices 144 will compress as they pass through opening 102 if such compression requires less force than expansion of the anchor 90. As the distal end 94 of the anchor 90 is pulled up proximally, the body of the anchor begins to expand as shown in FIG. 12. As shown in FIG. 14, the suture 140 may comprise a plurality of unidirectional locking devices 144. When the unidirectional locking devices 144 pass through the opening 100, the anchor 90 will compress (e.g., become smaller) in the insertion direction X and may expand (e.g., become larger) in the second direction Z and/or the third direction Y.

Figure 14:
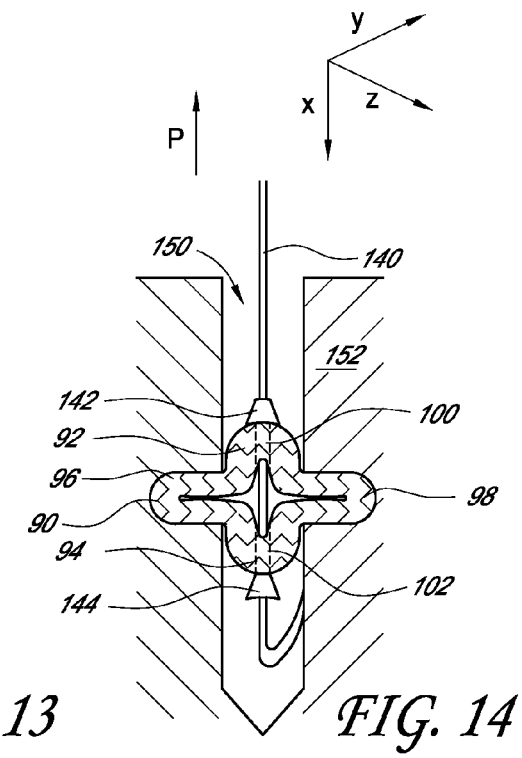
FIG. 14 shows the soft anchor of FIG. 13 in a deployed state.

Then, the suture 140 is further pulled, such that a unidirectional locking device 144 passes both the opening 102 in the distal end 94 and opening 100 the proximal end 92 of the anchor 90 as shown in FIG. 14. In this configuration, the anchor 90 is deployed or in the second state, and the suture 140 cannot pass backward in the insertion direction or locking direction through the anchor 90 because a locking surface 149 of the unidirectional locking device 144 prevents movement. In some embodiments, the unidirectional locking devices 144 have passed the opening 100 in the proximal end 92 and the locking surface 149 abuts against the proximal end 92 of the anchor 90. In some embodiments, the unidirectional locking devices 144 has passed the opening 102 in the distal end 94 and the locking surface 149 abuts against the inner surface of the distal end 94 of the anchor 90. The openings 100, 102 of the anchor 90 are adapted to let pass the suture 140 including the unidirectional locking devices 144 only in one direction. The suture 140 is able to be pulled through the anchor 90 in one direction (e.g., the passing direction P), but it cannot be pulled through the opposite direction.

In other words, as the suture 140 with the unidirectional locking devices 144, for example having the knotted, barbed or woven locking geometry described herein, is pulled through the anchor 90 it begins to lock itself on the proximal side of the anchor 90. Each time a unidirectional locking device 144 of the suture 140 is pulled through the proximal end 92 of the anchor 90, the locking surface 149 locks itself in that position and the anchor 90 holds tension on a soft tissue, which was fixed with the suture 140. The unidirectional locking devices 144 on the suture 140 lock the suture 140 in place. The anchor 90 coupled to the suture 140 can be compressed against soft tissue thereby retaining the anchor 90 in the bore 170 by friction fit. Or, in some embodiments the anchor 90, as it expands radially, may crush the cancellous bone that it comes into contact with, as shown in FIG. 14.

Thus, the anchor 90 is fixed in the bone 152 without being able to be pulled out of the bore 150. FIG. 14 shows the anchor 90 in one collapsed state, for example, a collapsed state without external constraints from the bone 152 (e.g., displacing or compressing the bone that the anchor 90 contacts). In some embodiments, the anchor 90 may cause less deformation of the bone 152 (e.g., slight deformation). In some embodiments, the anchor 90 causes no deformation of the bone 152 and rather abuts the surface of the bore 150 causing a frictional fit between the anchor 90 and the bore 150. The ends of the suture 140 extending form the bore 150 can be coupled to another structure, such as soft tissue (not shown).

According to another embodiment, multiple sutures, for example two sutures 140, are intended to be pulled through the anchor 90.

In other words, the geometry of the suture 140 causes the anchor 90 to deploy or collapse and lock into a closed position or second state and hold tension on the suture 140.

FIGS. 15 to 26 show several steps for proceeding to repair of a torn tissue, for example a torn labrum.

In steps of a method, shown in FIGS. 15 and 16, a suture 160 is passed around a piece of a soft tissue 162, for example a labrum. The bone 168 is also shown.

After the suture has been passed around the soft tissue 162, as shown in FIG. 16, both tails 164 of the suture 160 are passed through the openings 100, 102 at the distal and proximal ends 92, 94 of the anchor 90. For example, the anchor 90 according to FIG. 6 is shown in FIG. 17, but other anchors described herein may be used. In FIG. 17, the anchor 90 is already attached to the insertion device 130 in its first state prior to passing the tails 164 through the openings 100, 102. For example, the tube 135, in particular the distal end of the tube 135, is adapted to come in contact with the proximal end 92 of the anchor 90. The shaft 137 extends out of the tube 135 and come in contact with the distal end 94 of the anchor 90. For example, the distal end 94 of the anchor 90 is engaged by the shaped portion 138 of the shaft 137, as shown in FIG. 17.

A hole is drilled into the bone 168, for example a glenoid, to form a bore 170. As shown in FIGS. 18 and 19, the anchor 90 is inserted in the bore 170 using the insertion device 130. In an embodiment shown in FIG. 20, a mallet 171 may be used to fully insert in the anchor 90 into the bore 170, as shown by the downward arrows. This may be determined by abutting the insertion device 130 on the bone 168. The user can hold a handle 173 of an inserter shaft 172 while using the mallet 171.

FIG. 21 shows a section through the bone 168 and the insertion device 130 and the bore 170. The insertion device 130 comprising the suture 160, the tube 135 and the shaft 137 can pass through the handle 173. The suture 160 is passed around the soft tissue 162. The suture 160 is passed through the insertion device 130 such the tails of the suture 160 pass in the same direction, passing direction P, through the anchor 90 from the distal end 94 toward the proximal end 92.

Figure 27:
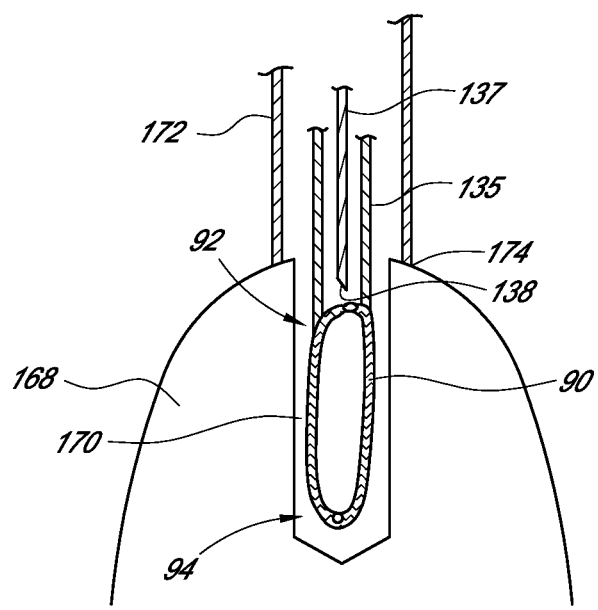
FIG. 27 shows a simplified enlarged view of FIG. 21 using the inserter device of FIGS. 9 and 10.

FIG. 27 shows a simplified enlarged view of FIG. 21 without the suture 160. The tube 135 and optionally the distal end 138 of the shaft 137 of the insertion device 130 holds the anchor 90 in place while it is in the bore 170. The shaft 137 is already pulled back through the anchor 90 into the tube 135 for the deployment of the anchor 90. As it can be seen from FIGS. 21 and 27, the anchor 90 is inserted into the bore 170 while in its first state. Referring to FIGS. 21 and 27, when the suture 160 is pulled, the anchor 90 stays in place due to the tube 135 of the insertion device 130, the tip 138 of the shaft 137 and/or the tip 174 of the inserter shaft 172.

In some methods, shown in FIG. 22, the suture tails or strands 164 of the suture 160 are pulled and begin to progress through the anchor 90. The suture can be pulled while the tube 135 holds the proximal end 92 of the anchor 90 in place, as shown in FIG. 27. In some methods, the handle 134 is coupled to the suture 160 and pulled in the passing direction P. Referring back to FIG. 9, the suture 160 may pass through opening 136 in the insertion device 130. A cap 163 can secure the suture to the handle 134, such that upward movement of the handle causes the suture 160 to pass in the passing direction P. In some methods, only the suture 160 is pulled and the handle 134 remains stationary.

Figure 23:
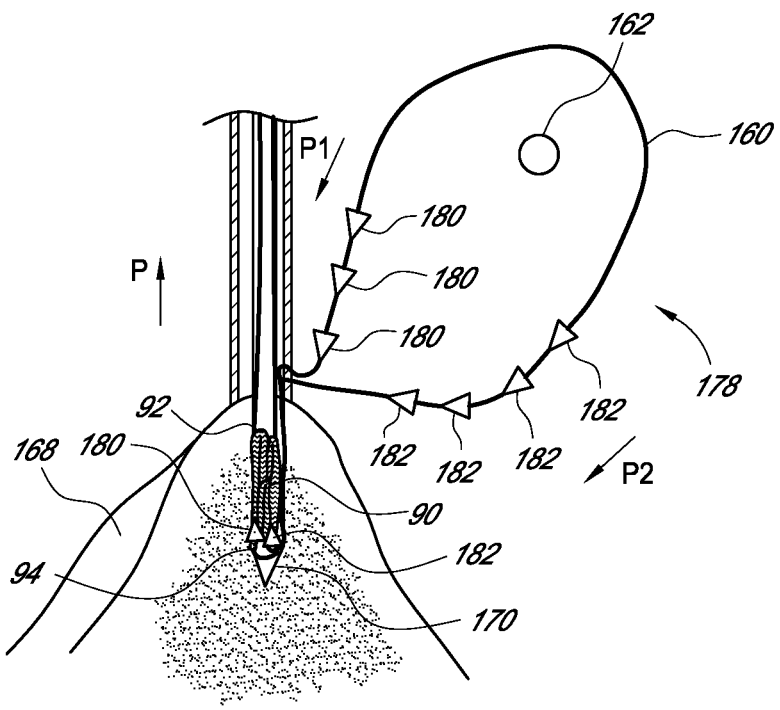

In FIG. 23 the suture 160 is shown in more detail. In the present case, the suture 160 comprises unidirectional locking devices 180, 182 according to an embodiment disclosed herein. The suture 160 has two groups of unidirectional locking devices, being directed in opposite directions as shown in FIGS. 4 and 23, and defining respectively a section of the suture 160. In other words, the suture 160 includes two sections, namely a first section with unidirectional locking devices 180 having a first passing direction P1 and a second section unidirectional locking devices 182 having a second passing direction P2, as shown in FIG. 23. In some techniques, a section of the suture 160 between the first second and the second section forms a loop around soft tissue 162. In some techniques, as shown in FIGS. 15-16, the suture 160 is looped around the soft tissue 162 before engaging the anchor 90.

The suture 160 has a loop 178, which is arranged around the soft tissue 162, in this case the labrum, which should be fixed to the bone 168. The suture 160 comprises a plurality of unidirectional locking devices 180, 182 comprising a first group of unidirectional locking devices 180 defining a first section and a second group of unidirectional locking devices 182 defining a second section. The first and the second sections of the suture 160 have opposite passing directions P1, P2, as explained already with respect to FIG. 4 and above. The unidirectional locking devices 180, 182 can have similar features to 14, 24, 34, 44, 46 of embodiments shown in FIGS. 1-4. For example, the unidirectional locking devices 180, 182 may have a woven conical geometry, as shown in FIG. 1. Both sections of the suture 160 pass in the same direction, passing direction P, through the anchor 90, namely from the distal end 94 to the proximal end 92 of the anchor 90. The unidirectional locking devices 180, 182 pass through the anchor 90 and the anchor 90 begins to compress and to extend in a plane orthogonal to the insertion direction X as it is shown in FIGS. 11 to 14. The anchor 90 transitions from the first state to the second state by the same method as described with respect to FIGS. 11-14. The suture 160 is tensioned around the soft tissue 162 as needed by passing the suture 160 through the anchor 90.

Figure 24:
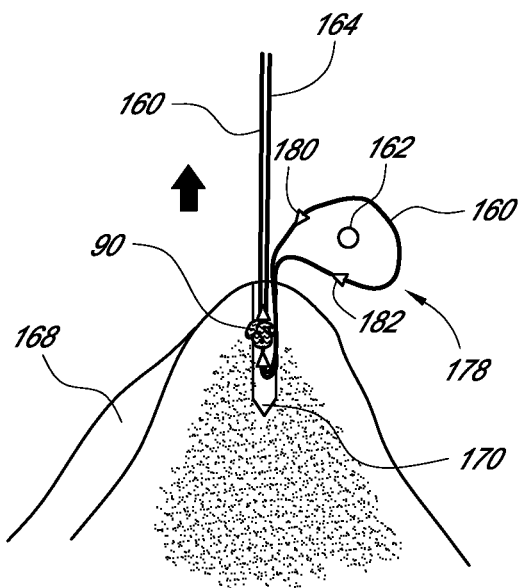

FIG. 24 shows the fully compressed anchor 90 locked into the bore 170 in the bone 168. In other words, as the suture 160 progresses through the anchor 90, the anchor 90 expands and locks itself to the bore 170. Each time the unidirectional locking devices 180, 182 pass through the anchor 90, the loop 178 around the soft tissue 162 decreases in size and pulls tighter on the soft tissue 162. The tension on the soft tissue 162 is locked in place due to the unidirectional locking devices 180, 182 on the suture 160. The tube 135 of the inserter 130 is removed from the bore after the anchor 90 is deployed and sutures 160 are in place.

Figures 25, 26:
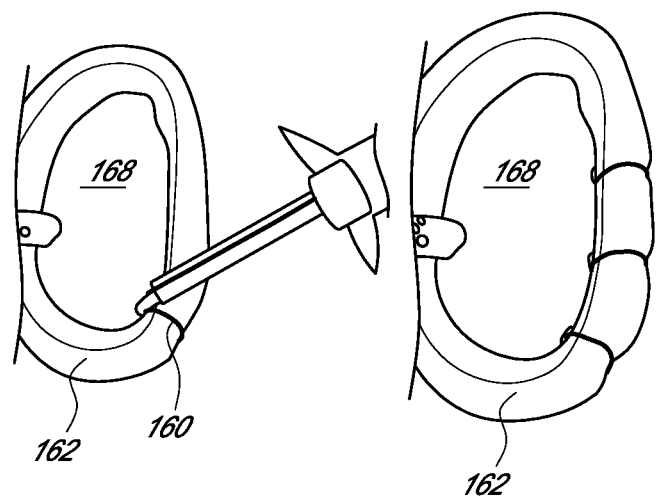

FIG. 25 shows the sutures 160 tensioned around the soft tissue 162. In some embodiments, excess suture 160, such as the suture tails 164 shown in FIG. 24, are cut. In some embodiments, it is not necessary to knot both tails 164 of the suture 160 together to fix the soft tissue 162 to the bone 168 due to the unidirectional locking devices 180, 182.

The method for attaching a soft tissue 162 to a bone 168 can be repeated at several times to fix several locations of the soft tissue 162 as shown in FIG. 26, where a completed repair is shown.

In some embodiments, the anchor 90 may be preloaded with a suture for use in a standard tip (e.g., non cinchable) suture configuration. In other embodiments, as shown in FIGS. 15 to 26, the suture 160 is passed through the anchor 90 after it has been passed through a soft tissue 162 to be fixed to a bone.

FIGS. 28 and 29 show a further embodiment of an anchor 260 that may be used with a suture 280 according to an embodiment disclosed herein. The anchor 260 is shown in the second state. The suture 280 can include the unidirectional locking device 288. The unidirectional locking device 288 can have similar features to 14, 24, 34, 44, 46 of embodiments shown in FIGS. 1-4.

In some embodiments, a single piece anchor design could be altered to include multiple loop features that would allow for cinchability.

The anchor 260 corresponds substantially to the soft anchor 60 shown in FIG. 5. In some embodiments, the anchor 260 is knotless and woven from a suture. The anchor 260 has a proximal end 262 and a distal end 264. The proximal end 262 and distal end 264 are connected by two walls 266, 268. In the first state, the walls 266, 268 are arranged substantially parallel to each other, similar to walls 76, 78 shown in FIG. 5. In contrast to the embodiment shown in FIG. 5, in a section of the proximal end 262, at which the proximal end 262 merges with the two walls 266, 268, the anchor 260 comprises respectively two openings 270 opposing each other. In a section of the distal end 264, at which the distal end 264 merges with the two walls 266, 268, the anchor 260 comprises respectively two openings 272 opposing each other. In some embodiment, the anchor 260 may comprise more than respectively two opposite openings 270, 272.

The anchor 260 may be used with a suture 280 in several ways, two of them are shown in FIGS. 28 and 29.

The suture 280 may be, for example, similar to the suture 160 shown in the previous example. For example, the suture may comprise two sections having opposite passing directions P1 and P1, respectively in direction of the suture tails 282, 284. The suture 280 is provided in a loop 286 around a soft tissue. Both tails 282, 284 are then inserted first through both openings 272 at the distal end 264 and then, subsequently on the same side through both openings 270 at the proximal end 262, so that the suture passes in outside of the anchor 260 along one of the two walls, here the wall 268. When the tails 282, 284 of the suture 280 are pulled, both of the walls 266, 268 are folded. For example, the wall 268 is folded so that a proximal end 262 of the wall may abut a distal end 264 of the wall 268. The unidirectional locking devices 288 pass through the openings 272 at the distal end 264 and subsequently through the openings 270 at the proximal end 262. The unidirectional locking devices 288 pass through the openings 270, 272 and lock at one of the openings 270 at the proximal end 262 when the locking surface of the unidirectional locking devices 288 abuts the wall 266. In particular, the openings 272 of the distal end 264 are close to the openings 270 of the proximal end 262 of the anchor 260 when the suture 260 is tensioned thereby tensioning, the soft tissue in the loop 286.

FIG. 29 shows a different arrangement of the suture 280. The suture tails 282, 284 are first inserted through the openings 270 at the proximal end 262 in a first insertion direction ID. Then, the tails 282, 284 are passed around the distal end 264 anchor 260 toward openings 272. Subsequently, the tails 282, 284 are inserted at the distal end 264 through both opposing openings 272, and reinserted through the opposing openings 270 at the proximal end 262 in an opposite direction to the insertion direction ID. The unidirectional locking devices 288 pass through the openings 270, 272 and lock at one of the openings 270 at the proximal end 262 when the locking surface of the unidirectional locking devices 288 abuts the wall 266. In particular, the openings 272 of the distal end 264 are close to the openings 270 of the proximal end 262 of the anchor 260 when the suture 260 is tensioned, thereby tensioning the soft tissue in the loop 286.

FIGS. 30 and 31 show further embodiments of an anchor 290. The anchor 290 can be similar to anchor 110 of FIGS. 7 and 8. In FIG. 30 the anchor 290 is shown in the first state. The same reference numbers refer to the same features as in FIGS. 7 and 8. The proximal end 112 includes the opening 116 and the distal end 114 includes the opening 118. The wall 120 connects the proximal end 112 with the distal end 114.

The embodiment of the soft anchor 290 of FIGS. 30 and 31 further comprises a bar 292 traversing diametrically the opening 118 at the distal end 114, spanning the inner surface of the wall 120. The bar 292 is provided to hold two soft suture rings 294, 296. The soft suture rings 294, 296 can be configured substantially similar to anchors described herein. The rings 294, 296 encircle the bar 292. The rings 294, 296 are not otherwise connected to the bar 262 allowing for longitudinal movement in the insertion direction X. In some embodiments, the rings 294, 296 have substantially the same diameter, extension and/or circumferential lengths.

FIG. 31 shows the soft anchor 290 in the second state. A suture 300 is threaded in a manner similar to FIG. 29. The suture 300 can have similar features to sutures described herein or can have a smooth outer surface without locking devices. The tails 382, 384 of a suture 300 are first passed through the first ring 294 in a first insertion direction ID. Then the tails 382, 384 are then passed around and through the second ring 296. Subsequently, the tails 382, 384 are then passed in the reverse direction opposing the first insertion direction ID through the first ring 294. Finally, both tails 382, 384 of the suture 300 are pulled, and the anchor 290 starts to collapse to reach the second state. In some embodiments, the suture 300 is held in place by the internal friction of between the suture 300 and the rings 294, 296. In other embodiment, one or more of the rings 294, 296 have openings 100, 102 similar to FIG. 11. The suture 300 can include unidirectional locking devices (not shown). The rings 294, 296 transition from the first state to the second state by the same method as described with respect to FIGS. 11-14. Thus, the anchor 290 is cinched. Thus, according to the invention a knotless suture fixation is shown. Such a knotless configuration will allow the soft anchor to be used in multiple indications.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

While embodiments of this invention have been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A suture fixation system, comprising:
    a suture;
    a soft anchor comprising:
        a proximal end comprising an opening, a distal end comprising an opening and a connecting portion extending therebetween;
        a bar traversing diametrically at least one of the openings; and
        a first locking element and a second locking element disposed around the bar,
    wherein the suture is configured to pass through the first locking element, around the second locking element, and through the first locking element to cause the soft anchor to deploy from a first insertion state to a second locking state.

2. The suture fixation system of claim 1, wherein the soft anchor has an elongated shape in the first insertion state.

3. The suture fixation system of claim 1, wherein the soft anchor has a collapsed shape in the second locking state.

4. The suture fixation system of claim 1, wherein the soft anchor has an increased diameter in the second locking state.

5. The suture fixation system of claim 1, wherein the soft anchor is configured to expand in a plane orthogonal to an insertion direction in the second locking state.

6. The suture fixation system of claim 1, wherein at least one of the first locking element and the second locking element is a ring.

7. The suture fixation system of claim 1, wherein at least one of the first locking element and the second locking element is a soft suture ring.

8. The suture fixation system of claim 1, wherein at least one of the first locking element and the second locking element is configured for longitudinal movement.

9. The suture fixation system of claim 1, wherein the first locking element and the second locking element have substantially the same diameter.

10. The suture fixation system of claim 1, wherein the first locking element and the second locking element have substantially the same extension relative to the bar.

11. The suture fixation system of claim 1, wherein the first locking element and the second locking element have substantially the same circumferential lengths.

12. The suture fixation system of claim 1, wherein the suture has a smooth outer surface.

13. The suture fixation system of claim 1, wherein the suture comprises a locking device.

14. The suture fixation system of claim 1, wherein the suture comprises a unidirectional locking device.

15. The suture fixation system of claim 1, wherein the suture comprises two segments and an arc therebetween, wherein the two segments are configured to pass through the first locking element and around the second locking element to exert a force on the first locking element and the second locking element when the suture is pulled.

16. The suture fixation system of claim 15, wherein the soft anchor is configured to collapse to reach the second locking state when the suture is pulled.

17. The suture fixation system of claim 1, wherein the suture fixation system is a knotless suture fixation system.

18. The suture fixation system of claim 1, wherein the soft anchor woven from a suture.

19. The suture fixation system of claim 1, wherein the soft anchor is cylindrical in the first insertion state.

20. The suture fixation system of claim 1, wherein the proximal end and the distal end are configured to be moved toward each other in the second locking state.

21. The suture fixation system of claim 1, wherein the soft anchor is configured to be locked in a bore in the second locking state.

22. The suture fixation system of claim 1, wherein at least one of the first locking element and the second locking element is ring shaped.

23. The suture fixation system of claim 1, wherein at least one of the first locking element and the second locking element is configured for longitudinal movement along an axis of the soft anchor.

24. The suture fixation system of claim 1, wherein at least one of the first locking element and the second locking element is configured for movement in a direction of insertion of the soft anchor.

25. The suture fixation system of claim 1, wherein at least one of the first locking element and the second locking element is enclosed.

26. The suture fixation system of claim 1, wherein at least one of the soft anchor, the first locking element, and the second locking element is woven.

* * * * *

UNITED STATES PATENT AND TRADEMARK OFFICE
CERTIFICATE OF CORRECTION

| | |
|---|---|
| PATENT NO. | : 10,016,192 B2 |
| APPLICATION NO. | : 14/304235 |
| DATED | : July 10, 2018 |
| INVENTOR(S) | : Clinton Andrew Beck |

Page 1 of 1

It is certified that error appears in the above-identified patent and that said Letters Patent is hereby corrected as shown below:

In the Specification

In Column 2, Line 1, change "is(are)" to --is (are)--

In Column 9, Line 27, change "the the" to --the--

Signed and Sealed this
Eleventh Day of December, 2018

Andrei Iancu
*Director of the United States Patent and Trademark Office*